US00PP26054P3

(12) United States Plant Patent
Bradford et al.

(10) Patent No.: US PP26,054 P3
(45) Date of Patent: Nov. 10, 2015

(54) INTERSPECIFIC TREE NAMED 'BLACKRED XX'

(50) Latin Name: ***Prunus* sp.**
Varietal Denomination: Blackred XX

(71) Applicants: Lowell Glen Bradford, Le Grand, CA (US); Jon Michael Quisenberry, Merced, CA (US)

(72) Inventors: Lowell Glen Bradford, Le Grand, CA (US); Jon Michael Quisenberry, Merced, CA (US)

( * ) Notice: Subject to any disclaimer, the term of this patent is extended or adjusted under 35 U.S.C. 154(b) by 164 days.

(21) Appl. No.: 13/998,851

(22) Filed: Dec. 16, 2013

(65) Prior Publication Data

US 2015/0173268 P1 Jun. 18, 2015

(51) Int. Cl.
*A01H 5/08* (2006.01)

(52) U.S. Cl.
USPC ..... Plt./180

(58) Field of Classification Search
USPC ..... Plt./180
See application file for complete search history.

(56) References Cited

U.S. PATENT DOCUMENTS

PP14,220 P2 10/2003 Bradford
PP20,892 P2 3/2010 Bradford

*Primary Examiner* — Susan McCormick Ewoldt

(57) ABSTRACT

The present invention relates to an interspecific tree and more particularly to a new and distinct variety broadly characterized by a small size, weakly vigorous, hardy, and productive tree. Being self-unfruitful, the present variety requires cross pollination from an apricot, interspecific, or plum that blooms during the mid to late season. The present variety produces a heavy bloom with an abundant amount of pollen to entice good bee activity to facilitate pollination. The fruit matures under the ecological conditions described during mid October, with first picking on Oct. 10, 2013, and can hang on the tree for up to two weeks. The fruit is medium in size, black in skin color, clingstone in type, globose in shape, orange in flesh color, firm in texture, and excellent flavor in flavor.

1 Drawing Sheet

Botanical classification: *Prunus* sp.
Varietal denomination: 'BLACKRED XX'.

BACKGROUND OF THE VARIETY

In a continuing effort to improve the quality of shipping fruits, we, the inventors, typically hybridize a large number of peach, nectarine, plum, apricot, and cherry seedlings each year. We also grow a lesser number of open pollinated seeds of each of these fruits. The present invention relates to a new and distinct variety of interspecific tree which has been denominated varietally as 'Blackred XX'.

During a typical blooming season we isolate as seed parents both individual and groups of different plum trees by covering them with screen houses. A hive of bees is placed inside each such house, and bouquets to provide pollen from different plum, apricot, and interspecific hybrid trees are placed in buckets near the trees approximately every two days for the duration of the bloom. During 2007 one such house containing 'September Yummy' (U.S. Plant Pat. No. 14,220) plum tree was crossed by us in this manner. To pollinate this plum, we selected bouquets from several sources of apricot and interspecific trees without keeping specific written details. Upon reaching maturity the fruit from this plum tree was harvested and the seeds were removed, cracked, stratified and germinated as a group with the label "H12". They were grown as seedlings on their own root in our greenhouse and upon reaching dormancy transplanted to a cultivated area of our experimental orchard located near Le Grand, Calif. in Merced County (San Joaquin Valley). During the summer of 2010 the claimed variety was selected by us as a single plant from the group of seedlings described above. Subsequent to origination of the present variety of interspecific tree, we asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'September Yummy' plum (U.S. Plant Pat. No. 14,220), by being self-unfruitful, by blooming in the mid season, and by producing fruit that is firm and juicy, but is distinguished therefrom by producing fruit that is much sweeter in flavor, that is black instead of red in skin color, and that matures about thirty days later.

The present variety is most similar to 'Blackred XII' (U.S. Plant Pat. No. 20,892) interspecific tree, by being self-unfruitful, by being much less vigorous, and by producing fruit that is full black in skin color, nearly globose in shape, firm in texture, juicy and very sweet, but is distinguished therefrom by being less vigorous, by blooming about four days earlier and by producing fruit that is full orange in flesh color instead of red, that is smaller in size, and that matures about two weeks later.

SUMMARY OF VARIETY

The present interspecific variety is characterized by a small size, weakly vigorous, hardy, and productive tree. Being self-unfruitful, the present variety requires cross pollination from an apricot, interspecific, or plum that blooms during the mid to late season. The present variety produces a heavy bloom with an abundant amount of pollen to entice good bee activity to facilitate pollination. The fruit matures under the ecological conditions described during mid October, with first picking on Oct. 10, 2013, and can hang on the tree for up to two weeks. The fruit is medium in size, black in skin color, clingstone in type, globose in shape, orange in flesh color, firm in texture, and excellent flavor in flavor.

DRAWING

The accompanying photograph consists of four whole fruits positioned to display the characteristics of the skin color and form, a half fruit divided to reveal the flesh and stone, a seed, typical leaves, and two insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of firm ripe on Oct. 12, 2013, on the original tree during its sixth growing season. The flower and bud descriptions were developed during the previous blooming season. All major color code designations are by reference to the Inter-Society Color Council, National Bureau of Standards. Common color names are also used occasionally.

It is to be noted that the 2013 fruit season in California was very warm during the spring and the ripening times of almost all varieties were about ten days earlier than other years.

PARENTAGE

Seed parent: 'September Yummy' plum (U.S. Plant Pat. No. 14,220).

Pollen parent: Unknown.

TREE

Size: Small, reaching and maintaining a height of 7' [2.13 m.] and a spread of 4' [1.22 m.] after six growing seasons utilizing typical dormant pruning.

Vigor: Weak vigor, responding below average to irrigation and fertilization. The variety grows about 2' [0.61 m.] of surplus top-growth during the spring and summer. The plant should be grown on a standard commercial rootstock for production purposes.

Growth: Upright and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Medium productive, thinning usually necessary.

Fertility: Self-unfruitful, requiring cross pollination by a suitable mid seasonal blooming apricot, interspecific, or plum, such as 'Blackred XII' interspecific tree (U.S. Plant Pat. No. 20,892).

Bearing: Uncertain bearer.

Trunk:

*Size.*—Medium, reaching a maximum diameter of 3" [76.2 mm.] after the six growing season.

*Texture.*—Medium.

*Bark color.*—Brownish gray [64. brGy] with Strong brown [55. s.Br] crevices present.

Lenticels.—Approximate Number Per Square Inch: 15. Color: Light brown [57. l.Br]. Size: ⅛" [3.2 mm.] to ¼" [6.4 mm.]. Shape: Eye-shaped, elongated.

Branches:

*Size.*—Main scaffold is 1¼" [31.8 mm.] in diameter measured 12" above crotch. Maximum diameter of first hanger is ¾" [19.1 mm.].

*Texture.*—Smooth on first and second year wood, increasing roughness with age.

*Color.*—2nd Year Wood: Dark grayish brown [62. d.gy.Br] with Grayish brown [61. gy.Br] variegation and Brownish orange [54. brO] crevices present.

*Lenticels.*—Number Per Square Inch: About 40 on second year wood. Color: Light yellowish brown [76. l.yBr]. Average Size: 1/64" [0.4 mm.] to 1/16" [1.6 mm.]. Shape: Elongated, rectangular.

Leaves:

*Size.*—Medium. Average Length: 3¾" [95.3 mm.]. Average width: 2" [50.8 mm.].

*Arrangement.*—Alternate.

*Thickness.*—Medium.

*Form.*—Elliptical.

*Apex.*—Acuminate.

*Base.*—Some rounded, some acute with an average base angle of 55 degrees.

*Surface.*—Smooth.

*Color.*—Dorsal Surface: Moderate olive green [125. m.OlG]. Ventral Surface: Deep yellow green [118. deep YG].

*Margin.*—Finely serrate.

*Venation.*—Pinnately net veined.

*Petiole.*—Average Length: 1" [25.4 mm.]. Average Thickness: 1/16" [1.6 mm.]. Color: Brilliant yellow green [116. brill.YG].

*Stipules.*—Number: 2 per leaf, up to 6 per growing tip. Average Length: ¼" [6.4 mm.]. Color: Very dark yellowish green [138. v.d.yG] becoming Moderate brown [58. m.Br] with age.

*Glands.*—Number: 2 to 4 per leaf. Position: Slightly alternate, positioned at petiole and base of leaf blade. Size: Medium. Form: Globose. Color: Dark olive green [126. d.OlG] becoming Grayish brown [61. gy.Br] with age. Leaf buds: Pointed, medium.

Flower buds:

*Hardiness.*—Medium hardy, with respect to central California winters.

*Diameter.*—Typically 3/16" [4.8 mm.] 1 week before bloom.

*Length.*—Typically ⅜" [9.5 mm.] 1 week before bloom.

*Form.*—Not appressed.

*Surface.*—Pubescent.

*Tip color.*—White [263. White].

Flowers: Perfect, complete, perigynous, usually a single pistil, about thirty stamens, five sepals and petal locations alternately positioned.

*Average flower diameter.*—1" [25.4 mm.].

*Number of petals.*—Five, no double blossoms observed.

*Petal shape.*—Oval to circular.

*Petal margin.*—Entire, somewhat wavy with minute notches occasional.
*Average petal diameter.*—½" [12.7 mm.].
*Average petal length.*—9/16" [14.3 mm.].
*Petal apex.*—Rounded.
*Petal base.*—Obtuse.
*Petal color.*—White [263. White] on both sides.
*Anther color.*—Moderate orange [53. m.O] over a Brilliant yellow [83. brill.Y] center.
*Stigma color.*—Light greenish yellow [101. l.gY].
*Sepal color.*—Vivid greenish yellow [97. v.gY] on the outer surface with Light pink [4. l.Pk] tinting on the edge of a few.
*Sepal length.*—3/16" [4.8 mm.].
*Sepal width.*—5/32" [4.0 mm.].
*Sepal apex.*—Rounded to elliptical to match the width and length.
*Sepal margin.*—Fairly smooth to the naked eye, slightly serrate toward the apex when magnified.
*Average pistil length.*—11/16" [17.5 mm.].
*Average stamen length.*—9/16" [14.3 mm.].
*Fragrance.*—Moderate.
*Pollen production.*—Abundant, bee enticing.
*Bloom density.*—Heavy.
*Number per cluster.*—2 to 10, average 4.
*Blooming period.*—Mid season, two days before 'September Yummy®' plum (U.S. Plant Pat. No. 14,220).
*Onset of bloom.*—One percent on Feb. 25, 2013.
*Date of full bloom.*—Mar. 5, 2013.
*Duration of bloom.*—One to two weeks, dependent on ambient temperature.

FRUIT

Maturity when described: Firm ripe, Oct. 12, 2013.
Date of first picking: Oct. 10, 2013.
Date of last picking: Oct. 25, 2013.
Size: Uniform, Medium.
*Average diameter axially.*—2⅜" [60.3 mm.].
*Average diameter across cheek plane.*—2¼" [57.2 mm.].
*Average diameter across suture plane.*—2⅜" [60.3 mm.].
*Typical weight.*—4.0 ounces [113 grams].
Form: Uniform, globose, slightly asymmetrical.
*Longitudinal section form.*—Round to oval.
*Transverse section through diameter.*—Round.
Suture: An inconspicuous line located in a shallow groove extending from the base to the apex.
Ventral surface: Rounded, very slightly lipped toward base on both sides.
Lips: Slightly unequal.
Cavity: Flaring, elongated in suture plane, suture showing on one side.
*Depth.*—¼" [6.4 mm.].
*Breadth.*—9/16" [14.3 mm.].
Base: Truncate, cordate if viewed parallel to the suture.
Apex: Rounded with a slight protrusion on one side.
Pistil point: An inconspicuous Brilliant yellow green [116. brill.YG] dot.
Stem: Medium.
*Average length.*—7/16" [11.1 mm.].
*Average width.*—1/16" [1.6 mm.].
Skin:
*Thickness.*—Medium.
*Surface.*—Smooth.
*Tenacity.*—Tenacious to the flesh.
*Astringency.*—Slight.
*Tendency to crack.*—None observed during dry season.
*Color.*—Reddish black [24. rBlack] with minor Pale orange yellow [73. p.OY] freckling toward the base.
*Bloom.*—Abundant.
Flesh:
*Color.*—Strong orange yellow [68. s.OY].
*Surface of pit cavity.*—Covered with Deep orange yellow [69. deep OY] broken fibers when twisted from the stone.
*Amygdalin.*—Moderate.
*Juice.*—Moderate, rich.
*Texture.*—Firm, crisp.
*Fibers.*—Few, fine, tender.
*Ripens.*—Earliest toward the apex.
*Flavor.*—A balanced blend of acid and sugar, typically 25 brix.
*Aroma.*—Slight.
*Eating quality.*—Excellent.

STONE

Type: Clingstone.
Form: Oval.
Hilum: Narrow.
Base: Slightly oblique.
Apex: Acuminate.
Sides: Equal.
Surface: Very slightly furrowed near base.
External color of stone: Grayish yellowish brown [80. gy.yBr].
Pit wall color when cracked: Grayish yellow [90. gy.Y].
Cavity surface color: Grayish greenish yellow [105. gy.gY].
Average pit wall thickness: ⅛" [3.2 mm.].
Average width: 11/16" [17.5 mm.].
Average length: 13/16" [20.6 mm.].
Average breadth: ⅜" [9.5 mm.].
Tendency to split: None observed.
Kernel:
*Form.*—Oval.
*Skin color.*—Moderate yellowish brown [77. m.yBr] when first removed.
*Pellicle color.*—Deep yellowish brown [75. deep yBr].
*Vein color.*—Deep yellow green [118. deep YG].
*Taste.*—Bitter.
*Viable.*—Yes.
*Average width.*—⅜" [9.5 mm.].
*Average length.*—9/16" [14.3 mm.].
*Amygdalin.*—Scant.

USE

Market: Fresh market and long distance shipping.
Keeping quality: Good, fruit quality observed to remain in good condition after 30 days in standard cold room at 36° Fahrenheit [2° Celsius].
Shipping quality: Good.
Resistance to insects: No unusual susceptibilities noted.
Resistance to diseases: No unusual susceptibilities noted.

OTHER NOTES

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of interspecific *Prunus* sp. tree, substantially as illustrated and described, that is most similar to 'Blackred XII' (U.S. Plant Pat. No. 20,892) interspecific tree, by being self-unfruitful, by being much less vigorous, and by producing fruit that is full black in skin color, nearly globose in shape, firm in texture, juicy and very sweet, but is distinguished therefrom by being less vigorous, by blooming about four days earlier and by producing fruit that is full orange in flesh color instead of red, that is smaller in size, and that matures about two weeks later.

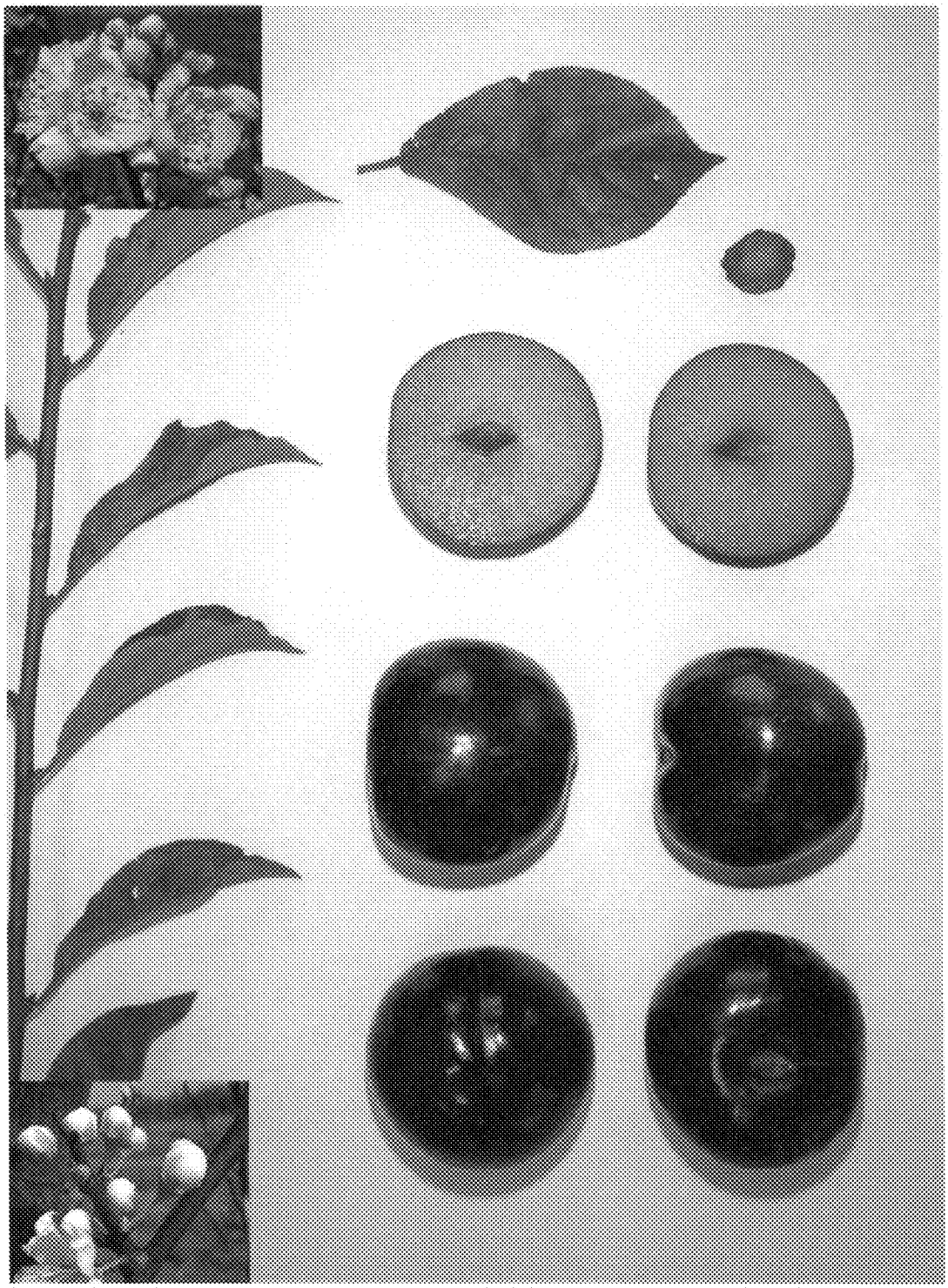

* * * * *